United States Patent [19]

Woon

[11] 4,318,407
[45] Mar. 9, 1982

[54] FOLDED TAMPON PLEDGET

[75] Inventor: Lin-Sun Woon, Appleton, Wis.

[73] Assignee: Kimberly-Clark Corporation, Neenah, Wis.

[21] Appl. No.: 182,097

[22] Filed: Aug. 28, 1980

[51] Int. Cl.³ ............................................. A61F 13/20
[52] U.S. Cl. ..................................... 128/285; 28/118; 28/120
[58] Field of Search ....................... 128/263, 270, 285; 28/118, 120

[56] References Cited

U.S. PATENT DOCUMENTS 3,011,495 12/1961 Brecht ..................................... 28/118
3,731,687 5/1973 Glassman ............................. 128/285
3,811,445 5/1974 Dostal ..................................... 28/120

Primary Examiner—C. Fred Rosenbaum
Attorney, Agent, or Firm—Howard Olevsky; William D. Herrick

[57] ABSTRACT

A tampon having a pledget consisting of two rectangular layers of absorbent material which have been overlaid along an edge of each of the layers and then folded along a line bisecting the angle formed by the juncture between the layers. The pledget thus produced has both inner and outer absorptive layers and a containment pocket formed of absorptive material in the fold area.

13 Claims, 4 Drawing Figures

FOLDED TAMPON PLEDGET

FIELD OF THE INVENTION

This invention relates to a novel tampon pledget and method for its assembly.

BACKGROUND OF THE INVENTION

Tampons, particularly those containing cellulosic absorbent material such as cotton or rayon, are generally made by the steps of aligning congruently rectangular layers of absorbent material, compressing these materials to a substantially bullet-shaped configuration of reduced size and then placing them into a tampon insertion tube for subsequent use. When the tampon pledget is in place, fluid uptake tends to swell the compressed pledget and, consequently, remove the compressed configuration.

Tampons made of conventional cellulosic material may slough fibers during use and are preferably wrapped with a fluid pervious outer wrap which prevents the fiber slough. The presence of this outer wrapping also defines the shape distortion possible when the absorbent material in the tampon swells as a result of fluid uptake. This wrap, therefore, effectively defines the surface area available for fluid uptake. As a practical matter, therefore, regardless of the amount of fluid uptake and the swelling that occurs as a result, the absorbent does not clearly return to its original layered state which existed prior to compression.

U.S. Pat. No. 4,212,301 issued to Russell L. Johnson; U.S. Pat. No. 3,397,695 issued to Joseph A. Voss and U.S. Pat. No. 3,731,687 issued to Jacob A. Glassman all generally disclose the concept of assembling a tampon made from strips of absorbent material which overlap each other in the approximate center of the strips. In the Voss patent, the tampon pledget when assembled resembles a series of aligned closely spaced tubes which are then compressed to form a series of fins. The Glassman patent teaches a tulip-shaped configuration for the pledget after expansion with the innermost portion of the tulip having a perforated fluid impervious layer. The concept of the Glassman patent relates to a means for utilizing a densified absorbent material which insures expansion upon wettability to form the tulip-shaped configuration. The pledget of this patent, however, requires several distinct layers of differing material along with a complex method of assembly.

The tampon of this application provides a pledget having increased exposed surface area of absorbent material, a containment pocket for the absorbent material, a tapered leading edge for ease of withdrawal and a wrapped surface to present fiber sloughing.

SUMMARY OF THE INVENTION

According to this invention, a tampon pledget is assembled by overlaying two rectangular surfaced absorbent layers at an edge of each so that the angle formed by the juncture is not greater than 90°. The rectangular surfaced absorbent layers are then folded about a line which approximately bisects the angle formed. After folding, the tampon pledget has two outer surfaces and two inner surfaces with the inner surfaces having an area identical to the outer surfaces in the unfolded portion. In the inner portion of the fold, a pocket having absorbent material at its interior is formed.

In surface configuration, the pledget has either four or five sides as will be described in more detail below. All of the sides are uneven in length and the longitudinal sides which, prior to folding, formed the equal, parallel, longest sides of the rectangular layers, remain parallel in the folded configuration. Each of these sides although now unequal in length, form right angles with a common transverse side. The shorter of the longitudinal sides also forms an obtuse angle with a fourth side.

DESCRIPTION OF THE DRAWINGS

The subject invention can be best understood by reference to the drawings in which.

Figure 1:
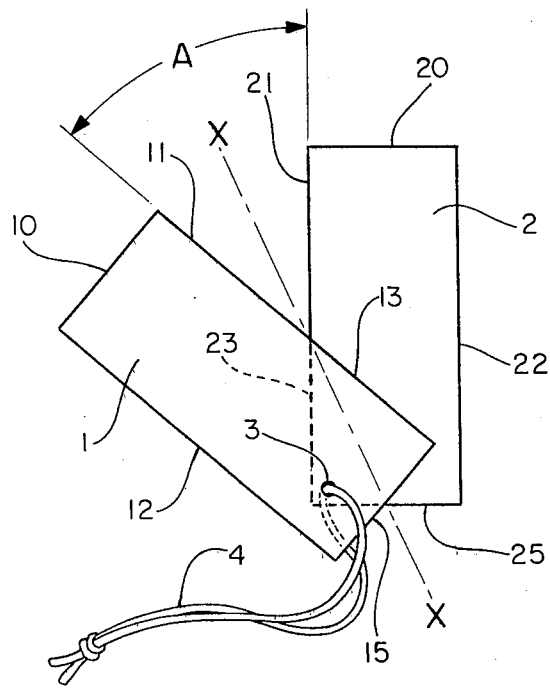
FIGS. 1 and 3 are planar views of two embodiments of the subject invention as oriented prior to folding and FIGS. 2 and 4 are plan views of the folded pledgets of FIGS. 1 and 3.

As can be seen from FIG. 1, two rectangular layers of absorbent material 1 and 2 respectively are overlaid at one edge. The inwardly facing sides 11 of absorbent layer 1 and 21 of absorbent layer 2 join to form an angle A which, according to this embodiment, is 30°. A fluid pervious outer wrap (not shown) is preferably utilized to cover the absorbent material if this material is fibrous in nature. The absorbent layers may be punctured at the overlap area and a withdrawal string 4 looped through the resultant orifice 3 or, this operation may be performed after the pledget is folded in the manner discussed below. The pledget is folded about axis line X—X which approximately bisects the angle A. The resultant pledget formed can be seen at FIG. 2 in which the absorbent component layer 2 rests essentially congruently on top of absorbent layer 1. The overlapping layers have been shown slightly off-center to illustrate the spacial relationship between the sides of each component in which the longitudinal sides 11 and 21 in the folded area become truncated in length and form an additional side 13 and 23 and an obtuse angle C of 165° where sides 11—21 and 23—13 intersect. The results of the fold also produce a truncated bottom segment line 15—25 which although still parallel to the top of the pledget 10—20 is substantially shorter than its original configuration. As can be seen from the drawing lines 20—10 and 12—22 are unchanged in shape or length from the unfolded edges of the individual layers of absorbent.

Figure 2:
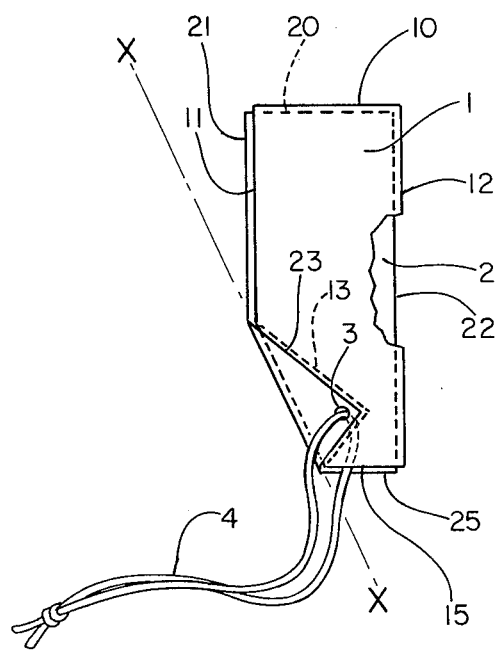
Figure 3:
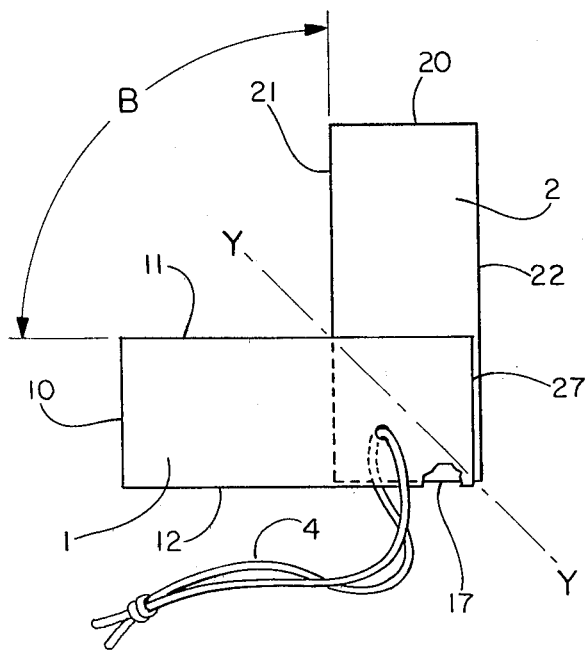
Figure 4:
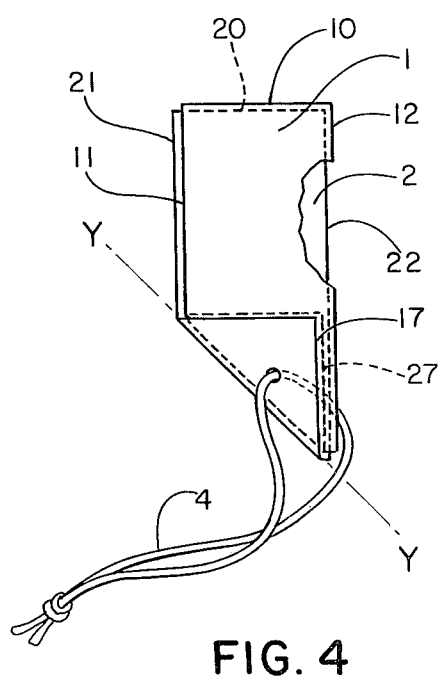

FIGS. 3 and 4 show overlap layers of absorbent material separated by a 90° angle B. As is the case above, the absorbent layers are folded about axis Y—Y which essentially bisects the angle formed by the intersection of sides 11 and 21 of absorbent material layers 1 and 2 respectively. The resultant pledget is shown at FIG. 4. In contrast to FIG. 2, FIG. 4 provides a four sided pledget rather than a five sided pledget and angle D is 135°. The side 17—27 which is not common to FIG. 2, upon compression, produces a wedge-shaped leading edge which simplifies withdrawal. It is of course worth noting that the pledget configurations shown in these figures are representative of the uncompressed state and after compression, a cylindroidal configuration with curved faces at edges 17—27, 15—25 and 23—13 will be produced.

The second embodiment is preferred not only because of the wedge-shaped configuration which provides a configuration which favors easier withdrawal but also because the containment pocket illustrated by the compressed area is larger and, if the individual layers are wrapped prior to folding, there is no need to wrap the area of the pocket on the pocket inner surface because fiber slough is virtually impossible.

As mentioned above, the hole for the withdrawal string and the string itself can be added either after the layers of absorbent have been overlapped or after the overlapping layers have been folded. The latter method is preferred because the withdrawal string tends to be perfectly centered when this option is chosen.

While this disclosure discusses the utilization of angles between the overlaid absorbent layers of 30° and 90°, angles intermediate of these values may also be utilized as would be apparent to those with reasonable skill in the art.

What is claimed is:

1. A folded tampon pledget comprising a flat surface having at least four sides, each of said sides being of uneven length, two of said sides being longitudinal, parallel and each forming a right angle with a common transverse side, and the shorter of said longitudinal, parallel sides forming an obtuse angle with a fourth side.

2. The tampon according to claim 1 wherein the pledget comprises at least two layers thereby forming both inner and outer surfaces with an overlapped edge of said layers.

3. The tampon according to claim 1 in which said pledget has five sides.

4. The tampon according to claim 1, 2 or 3 in which said angle is 165°.

5. The tampon according to claim 1 or 2 in which said angle is 135°.

6. The tampon according to claim 2 wherein a fluid permeable wrap overlays the outer surface of said layers and at least a portion of said inner surface.

7. A method for making a compressible settable tampon pledget which in its uncompressed state comprises a flat surface having at least four sides, each of said sides being of uneven length, two of said sides being longitudinal parallel and each forming a right angle with a common transverse side, and the shorter of said longitudinal, parallel sides forming an obtuse angle with a fourth side:
    (a) comprising partially overlapping a rectangular-surfaced layer of relatively stiff compressible cellulosic material with a second layer of rectangular surfaced cellulosic material at one end so that the angle formed by the intersection of the opposite edges of the respective layers are not greater than ninety degrees;
    (b) folding the two layers about a center line bisecting said angle; and
    (c) compressing said tampon.

8. The method of claim 7 in which withdrawal means are added prior to folding by placing an orifice in the approximate center of the overlaid layers and a string is looped underneath the overlapped edge and through said orifice prior to folding.

9. The method of claim 7 wherein an orifice is introduced in the overlaid area after folding.

10. The method according to claims 7, 8 or 9 wherein the angle formed is 30°.

11. The method according to claims 7, 8 or 9 wherein the angle formed is 90°.

12. The method according to claim 7 wherein the pledget layers are wrapped prior to overlaying.

13. The method according to claim 12 wherein the angle between the overlaid layers is 90°, and the wrap is slit on the portion which becomes the inner surface prior to folding.

* * * * *